United States Patent
Matsui et al.

(10) Patent No.: US 6,555,565 B2
(45) Date of Patent: Apr. 29, 2003

(54) APOPTOSIS INHIBITOR

(75) Inventors: Junji Matsui, Suita (JP); Naoki Tarui, Nara (JP); Yu Momose, Takarazuka (JP); Ken-ichi Naruo, Sanda (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/047,816

(22) Filed: Jan. 15, 2002

(65) Prior Publication Data

US 2002/0086883 A1 Jul. 4, 2002

Related U.S. Application Data

(62) Division of application No. 09/519,274, filed on Mar. 7, 2000, now Pat. No. 6,399,639, which is a continuation of application No. 09/272,747.
(60) Provisional application No. PCT/JP98/05178, filed on Nov. 18, 1998, now Pat. No. 6,087,384.

(30) Foreign Application Priority Data

Nov. 19, 1997 (JP) .............................................. 9-317926

(51) Int. Cl.$^7$ ........................................... A61K 31/427
(52) U.S. Cl. ..................................................... 514/369
(58) Field of Search ......................................... 514/369

(56) References Cited

U.S. PATENT DOCUMENTS

| | | | |
|---|---|---|---|
| 5,457,109 A | 10/1995 | Tammy et al. | |
| 5,602,133 A | 2/1997 | Tammy et al. | |
| 5,663,389 A | 9/1997 | Tammy et al. | |
| 5,726,055 A | 3/1998 | Hindley et al. | 435/280 |
| 5,968,960 A | 10/1999 | Schwartz | 514/369 |
| 6,242,196 B1 | 6/2001 | Spiegelman et al. | 435/7.1 |
| 2002/0035064 A1 * | 3/2002 | Robl | 514/12 |

FOREIGN PATENT DOCUMENTS

| | | |
|---|---|---|
| JP | 7-285864 A | 10/1995 |
| JP | 0753298 A | 1/1997 |
| JP | 09 291031 A | 11/1997 |
| WO | WO95/01979 | 1/1995 |
| WO | WO97/37656 | 10/1997 |

OTHER PUBLICATIONS

A. Okuno et al., "Effects of Thiazolidinendiones on Adipose Tissue . . . ," *The Saishin–Igaku*, Jun. '97, vol. 52 (6), pp. 1153–1160, with its English translation.

K. Suzuki, PhD and M. Yokota, MD, "Apoptosis–up to date–Chairman's introductory Remarks, 36th General Assembly of the Tokai–Hokuriku Branch, Japan Society of Clinical Pathology," *Japanese Journal of Clinical Pathology*, 45:603–605, 1997.

J. Larm et al., "(S)–5–Flurowillardiine–medicated neurotoxicity in cultured murine cortical neurones occurs via AMPA and kainate receptors," *European J. of Pharmacology* 314(1996) pp. 249–254.

H. Kizaki, "Apoptosis and Disease," *Igaku No Ayumi* (*J. of Clinical and Experimental Medicine*) 178(10): 712–716, 1996, with its English translation.

Y. Nagasaka et al., "The new oral hypoglycemic agent CS–045, . . . ," *Biochemical Pharmacology*, vol.50, No. 7, Sep. 28, 1995, pp. 1109–1111.

* cited by examiner

*Primary Examiner*—Robert Gerstl
(74) *Attorney, Agent, or Firm*—Mark Chao; Elaine M. Ramesh

(57) ABSTRACT

An apoptosis inhibitor which comprises a compound of the formula:

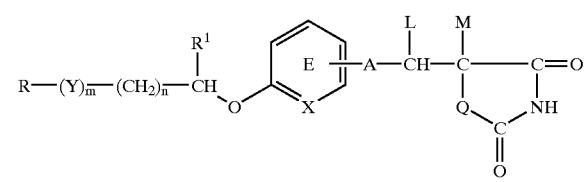

wherein R represents a hydrocarbon group that may be substituted or a heterocyclic group that may be substituted; Y represents a group of the formula: —CO—, —CH(OH)— or —NR$^3$— where R$^3$ represents an alkyl group that may be substituted; m is 0 or 1; n is 0, 1 or 2; X represents CH or N; A represents a chemical bond or a bivalent aliphatic hydrocarbon group having 1 to 7 carbon atoms; Q represents oxygen or sulfur; R$^1$ represents hydrogen or an alkyl group; ring E may have further 1 to 4 substituents, which may form a ring in combination with R$^1$; L and M respectively represent hydrogen or may be combined with each other to form a chemical bond; or a salt thereof, or a compound having an insulin sensitivity enhancing activity.

10 Claims, No Drawings

APOPTOSIS INHIBITOR

This application is a divisional of U.S. patent application Ser. No. 09/519,274, filed Mar. 7, 2000 and now U.S. Pat. No. 6,399,639 granted Jun. 4, 2002 which was a continuation of U.S. patent application Ser. No. 09/272,747 filed Mar. 15, 1999, now U.S. Pat. No. 6,087,384 granted Jul. 11, 2000, which was the National Phase of International Application for Patent Serial No. PCT/JP98/05178 filed Nov. 18, 1998.

TECHNICAL FIELD

The present invention relates to an apoptosis inhibitor which is useful as an agent for prophylaxis and treatment of a disease mediated by promotion of apoptosis.

BACKGROUND ART

Apoptosis means a physiological and active death of cells, abnormality of which is known to be closely related with occurrence of various diseases [Rinshou Byouri, vol.45, No.7, pp.603–605 (1997); Igaku no Ayumi, vol.178, No.10, pp.712–716 (1996)].

As compounds having an apoptosis inhibitory activity, there are known, for instance, (1-heteroazolyl-1-heterocyclyl)alkane derivatives (JP-A H8(1996)-512312), (3S,4aR,6R,8aR)-6-[2-(1H-tetrazol-5-yl)-ethyl-1,2,3,4,4a,5,6,7,8,8a-decahydroisoquinoline-3-carboxylic acid (European Journal of Pharmacology, vol. 314, pp. 249–254 (1996)) and the like.

Saishin igaku, vol. 52, No. 6, pp. 95–102 (1997), especially at page 100 describes "thiazolidines will, probably via PPARγ activities, promote differentiation from preadipocytes to adipocytes, remarkably increase the number of small adipocytes, and decrease the number of large adipocytes (apoptosis ??)", "thiazolidine derivatives affecting fatty tissues show remarkable effects to this types of insulin resistance", and shows "a mechanism of thiazolidine derivatives in changes of fatty tissues and improvement of insulin resistance (hypothesis)". However, these do not relate to an apoptosis inhibitory activity.

Drugs showing an apoptosis inhibitory activity can be used as an agent for prophylaxis and treatment of diseases which are thought to be mediated by promotion of apoptosis, such as viral diseases, neurodegenerative diseases, myelodysplasis, ischemic diseases and hepatic diseases. Therefore, development of such new types of drug is desired.

DISCLOSURE OF INVENTION

The inventors of the present invention, after various research about compounds having an apoptosis inhibitory activity, found, for the first time, that compounds having an insulin sensitivity enhancing activity, especially the compound of the formula:

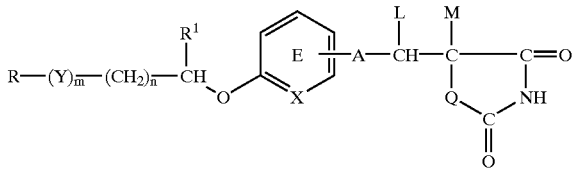

wherein R represents a hydrocarbon group that may be substituted or a heterocyclic group that may be substituted;
Y represents a group of the formula: —CO—, —CH(OH)— or —NR³— where R³ represents an alkyl group that may be substituted; m is 0 or 1; n is 0, 1 or 2; X represents CH or N; A represents a chemical bond or a bivalent aliphatic hydrocarbon group having 1 to 7 carbon atoms; Q represents oxygen or sulfur; R¹ represents hydrogen or an alkyl group; ring E may have further 1 to 4 substituents, which may form a ring in combination with R¹; L and M respectively represent hydrogen or may be combined with each other to form a chemical bond; or a salt thereof; which are characterized by azolidine and a particular side chain thereto, unexpectedly showed an excellent apoptosis inhibitory activity based on the characteristic chemical structure, and that it was useful as an agent for prophylaxis and treatment of diseases which are thought to be mediated by promotion of apoptosis. Based on this finding, the present invention has been completed.

The present invention relates to (1) An apoptosis inhibitor which comprises a compound represented by the formula (I);

(2) An apoptosis inhibitor according to the above (1), wherein the heterocyclic group represented by R is a 5- to 7-membered monocyclic and heterocyclic group containing 1 to 4 hetero-atoms selected from oxygen, sulfur and nitrogen in addition to carbon as ring members or its condensed heterocyclic group;

(3) An apoptosis inhibitor according to the above (1), wherein R represents a heterocyclic group that may be substituted;

(4) An apoptosis inhibitor according to the above (3), wherein the heterocyclic group is pyridyl, oxazolyl, thiazolyl or triazolyl;

(5) An apoptosis inhibitor according to the above (1), wherein the partial structural formula:

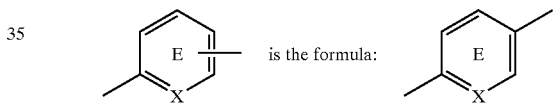

(6) An apoptosis inhibitor according to the above (1), wherein X represents CH;

(7) An apoptosis inhibitor according to the above (1), wherein R¹ represents hydrogen;

(8) An apoptosis inhibitor according to the above (1), wherein L and M respectively represent hydrogen;

(9) An apoptosis inhibitor which comprises a compound having an insulin sensitivity enhancing activity;

(10) An apoptosis inhibitor according to the above (1), which is an agent for prophylaxis or treatment of a neurodegenerative disease;

(11) An apoptosis inhibitor according to the above (1), which comprises pioglitazone or its salt;

(12) An apoptosis inhibitor according to the above (1), which comprises troglitazone or its salt;

(13) An apoptosis inhibitor according to the above (1), which comprises rosiglitazone or its salt;

(14) Method for inhibiting apoptosis in a mammal, which comprises administering to said mammal an effective amount of a compound or a salt as defined in the above (1);

(15) Method for treating or preventing a disease mediated by promotion of apoptosis in a mammal in need thereof, which comprises administering to said mammal an effective amount of a compound or a salt as defined in the above (1);

(16) Use of a compound or a salt as defined in the above (1) for the manufacture of an agent for prophylaxis or treatment of a disease mediated by promotion of apoptosis;

(17) Method for inhibiting apoptosis in a mammal, which comprises administering to said mammal an effective amount of a compound having an insulin sensitivity enhancing activity;

(18) Method for treating or preventing a disease mediated by promotion of apoptosis in a mammal in need thereof, which comprises administering to said mammal an effective amount of a compound having an insulin sensitivity enhancing activity; and

(19) Use of a compound having an insulin sensitivity enhancing activity for the manufacture of an agent for prophylaxis or treatment of a disease mediated by promotion of apoptosis.

The compound used in the present invention is not limited as long as it is a compound having an insulin sensitivity enhancing activity. Especially preferred is the compound represented by the formula (I) or salt thereof. Substituents in the formula (I) are explained below.

Referring to the hydrocarbon group that may be substituted for R, the hydrocarbon group includes aliphatic hydrocarbon groups, alicyclic hydrocarbon groups, alicyclic-aliphatic hydrocarbon groups, aromatic-aliphatic hydrocarbon groups, and aromatic hydrocarbon groups. The number of carbon atoms constituting such hydrocarbon groups is preferably 1 to 14.

The aliphatic hydrocarbon group is preferably a $C_{1-8}$ aliphatic hydrocarbon group. The aliphatic hydrocarbon group includes saturated $C_{1-8}$ aliphatic hydrocarbon groups (e.g. alkyl groups) such as methyl, ethyl, propyl, isopropyl, butyl, isobutyl, sec-butyl, t-butyl, pentyl, isopentyl, neopentyl, t-pentyl, hexyl, isohexyl, heptyl, and octyl; and unsaturated $C_{2-8}$ aliphatic hydrocarbon groups (e.g. alkenyl, alkadienyl, alkynyl, and alkadiynyl groups) such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, and 1-octynyl.

The alicyclic hydrocarbon group is preferably a $C_{3-7}$ alicyclic hydrocarbon group. The alicyclic hydrocarbon group includes saturated $C_{3-7}$ alicyclic hydrocarbon groups (e.g. cycloalkyl groups) such as cyclopropyl, cyclobutyl, cyclopentyl, cyclohexyl, cycloheptyl, etc. and unsaturated $C_{5-7}$ alicyclic hydrocarbon groups (e.g. cycloalkenyl groups and cycloalkadienyl groups) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, and 2,4-cycloheptadienyl.

The alicyclic-aliphatic hydrocarbon group is a group consisting of the above-described alicyclic hydrocarbon group and aliphatic hydrocarbon group (e.g. cycloalkyl-alkyl and cycloalkenyl-alkyl groups) and is preferably a $C_{4-9}$ alicyclic-aliphatic hydrocarbon group. Specifically, the alicyclic-aliphatic hydrocarbon group includes cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, etc.

The aromatic-aliphatic hydrocarbon group is preferably a $C_{7-13}$ aromatic-aliphatic hydrocarbon group (e.g. aralkyl and aryl-alkenyl groups). The aromatic-aliphatic hydrocarbon group includes $C_{7-9}$ phenylalkyl such as benzyl, phenethyl, 1-phenylethyl, 3-phenylpropyl, 2-phenylpropyl and 1-phenylpropyl; $C_{11-13}$-naphthylalkyl such as α-naphthylmethyl, α-naphthylethyl, β-naphthylmethyl, and β-naphthylethyl; $C_{8-10}$ phenylalkenyl such as styryl and 4-phenyl-1,3-butadienyl; and $C_{12-13}$ naphthylalkenyl such as 2-(2-naphthyl)vinyl.

The aromatic hydrocarbon group is preferably a $C_{6-14}$ aromatic hydrocarbon group (e.g. aryl groups). The aromatic hydrocarbon group includes phenyl and naphthyl (α-naphthyl, β-naphthyl).

Referring to the formula (I), the heterocyclic group in a heterocyclic group that may be substituted for R is a 5- to 7-membered monocyclic and heterocyclic group containing 1 to 4 hetero-atoms selected from oxygen, sulfur, and nitrogen in addition to carbon as ring members or its condensed heterocyclic group. The condensed heterocyclic group may for example be one consisting of such a 5- to 7-membered monocyclic and heterocyclic group and a 6-membered ring containing 1 or 2 nitrogen atoms, a benzene ring, or a 5-membered ring containing one sulfur atom.

Specifically the heterocyclic group includes 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl, benzopyranyl and 3,4-dihydrobenzopyran-2-yl. The preferred heterocyclic group is pyridyl, oxazolyl, thiazolyl, or triazolyl group.

Referring to the formula (I), the hydrocarbon group and heterocyclic group for R may respectively have 1 to 5, preferably 1 to 3 substituents at substitutable positions. Such substituents include for example aliphatic hydrocarbon groups, alicyclic hydrocarbon groups, aryl groups, aromatic heterocyclic groups, non-aromatic heterocyclic groups, halogen, nitro, amino group that may be substituted, acyl group that may be substituted, hydroxy group that may be substituted, thiol group that may be substituted, and carboxyl group that may be esterified.

The aliphatic hydrocarbon group includes straight-chain or branched aliphatic hydrocarbon groups having 1 to 15 carbon atoms, such as alkyl groups, alkenyl groups, and alkynyl groups.

The preferred alkyl group is a $C_{1-10}$ alkyl group, such as methyl, ethyl, propyl, isopropyl, butyl, isobutyl, sec-butyl, t-butyl, pentyl, isopentyl, neopentyl, t-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, and decyl.

The preferred alkenyl group is a $C_{2-10}$ alkenyl group, such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

The preferred alkynyl group is a $C_{2-10}$ alkynyl group, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

The alicyclic hydrocarbon group includes saturated and unsaturated alicyclic hydrocarbon groups having 3 to 12 carbon atoms, such as cycloalkyl groups, cycloalkenyl groups, and cycloalkadienyl groups.

The preferred cycloalkyl group is a $C_{3-10}$ cycloalkyl group, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, and bicyclo[4.3.1]decyl.

The preferred cycloalkenyl group is a $C_{3-10}$ cycloalkenyl group, such as 2-cyclopenten-1-yl, 3-cyclopenten-1-yl, 2-cyclohexen-1-yl, and 3-cyclohexen-1-yl.

The preferred cycloalkadienyl group is a $C_{4-10}$ cycloalkadienyl group, such as 2,4-cyclopentadien-1-yl, 2,4-cyclohexadien-1-yl, 2,5-cyclohexadien-1-yl.

The term "aryl group" means a monocyclic or condensed polycyclic aromatic hydrocarbon group. As preferred examples, $C_{6-14}$ aryl groups such as phenyl, naphthyl, anthryl, phenanthryl, acenaphthylenyl can be mentioned. Particularly preferred are phenyl, 1-naphthyl, and 2-naphthyl.

The preferred aromatic heterocyclic group includes 5- to 7-membered monocyclic aromatic heterocyclic groups containing 1 to 4 hetero-atoms selected from oxygen, sulfur, and nitrogen in addition to carbon as ring members, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, and triazinyl; and bicyclic or tricyclic condensed aromatic heterocyclic groups containing 1 to 5 hetero-atoms selected from oxygen, sulfur, and nitrogen in addition to carbon as ring members, such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

The preferred non-aromatic heterocyclic group includes oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino, morpholino, and thiomorpholino.

The halogen includes fluorine, chlorine, bromine, and iodine, and is preferably fluorine or chlorine.

The amino group that may be substituted includes amino (—NH$_2$) that may be mono- or di-substituted by, for example, $C_{1-10}$ alkyl groups, $C_{3-10}$ cycloalkyl groups, $C_{2-10}$ alkenyl groups, $C_{3-10}$ cycloalkenyl groups, $C_{1-13}$ acyl groups (e.g. $C_{2-10}$ alkanoyl groups, $C_{7-13}$ arylcarbonyl groups), or $C_{6-12}$ aryl groups. As examples of the substituted amino group, there can be mentioned methylamino, dimethylamino, ethylamino, diethylamino, dibutylamino, diallylamino, cyclohexylamino, acetylamino, propionylamino, benzoylamino, phenylamino, and N-methyl-N-phenylamino.

The acyl group in the acyl groups that may be substituted includes $C_{1-13}$ acyl groups. For example, formyl and groups formed between carbonyl and $C_{1-10}$ alkyl groups, $C_{3-10}$ cycloalkyl groups, $C_{2-10}$ alkenyl groups, $C_{3-10}$ cycloalkenyl groups, $C_{6-12}$ aryl groups, or aromatic heterocyclic groups (e.g. thienyl, furyl, pyridyl). The preferred acyl group includes acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, and nicotinoyl. The substituent in the substituted acyl groups includes $C_{1-3}$ alkyl, $C_{1-3}$ alkoxy groups, halogen (e.g. chlorine, fluorine, bromine, etc.), nitro, hydroxy, and amino.

Referring to the hydroxy group that may be substituted, the substituted hydroxy includes alkoxy, alkenyloxy, aralkyloxy, acyloxy, and aryloxy groups.

The preferred alkoxy group includes $C_{1-10}$ alkoxy groups, such as methoxy, ethoxy, propoxy, isopropoxy, butoxy, isobutoxy, sec-butoxy, t-butoxy, pentyloxy, isopentyloxy, neopentyloxy, hexyloxy, heptyloxy, nonyloxy, cyclobutoxy, cyclopentyloxy, and cyclohexyloxy.

The preferred alkenyloxy group includes $C_{2-10}$ alkenyloxy groups, such as allyloxy, crotyloxy, 2-pentenyloxy, 3-hexenyloxy, 2-cyclopentenylmethoxy, and 2-cyclohexenylmethoxy.

The preferred aralkyloxy group includes $C_{7-10}$ aralkyloxy groups, such as phenyl-$C_{1-4}$ alkyloxy (e.g. benzyloxy, phenethyloxy, etc.).

The preferred acyloxy group includes $C_{2-13}$ acyloxy groups, more preferably $C_{2-4}$ alkanoyloxy (e.g. acetyloxy, propionyloxy, butyryloxy, isobutyryloxy, etc.).

The preferred aryloxy group includes $C_{6-14}$ aryloxy groups, such as phenoxy, and naphthyloxy. This aryloxy group may have 1 or 2 substituents such as halogen (e.g. chlorine, fluorine, bromine, etc.). The substituted aryloxy group includes 4-chlorophenoxy.

Referring to the thiol group that may be substituted, the substituted thiol group includes alkylthio, cycloalkylthio, aralkylthio, and acylthio groups.

The preferred alkylthio group includes $C_{1-10}$ alkylthio groups, such as methylthio, ethylthio, propylthio, isopropylthio, butylthio, isobutylthio, sec-butylthio, t-butylthio, pentylthio, isopentylthio, neopentylthio, hexylthio, heptylthio, and nonylthio.

The preferred cycloalkylthio group includes $C_{3-10}$ cycloalkylthio groups such as cyclobutylthio, cyclopentylthio, and cyclohexylthio.

The preferred aralkylthio group includes $C_{7-10}$ aralkylthio groups, such as phenyl-$C_{1-4}$ alkylthio (e.g. benzylthio, phenethylthio, etc.).

The acylthio group is preferably a $C_{2-13}$ acylthio group, more preferably a $C_{2-4}$ alkanoylthio group (e.g. acetylthio, propionylthio, butyrylthio, isobutyrylthio, etc.).

The carboxyl group that may be esterified includes alkoxycarbonyl, aralkyloxycarbonyl, and aryloxycarbonyl groups.

The preferred alkoxycarbonyl group includes $C_{2-5}$ alkoxycarbonyl groups, such as methoxycarbonyl, ethoxycarbonyl, propoxycarbonyl, and butoxycarbonyl.

The preferred aralkyloxycarbonyl group includes $C_{8-10}$ aralkyloxycarbonyl groups, such as benzyloxycarbonyl.

The preferred aryloxycarbonyl group includes $C_{7-15}$ aryloxycarbonyl groups, such as phenoxycarbonyl, and p-tolyloxycarbonyl.

The preferred substituent on the hydrocarbon or heterocyclic group for R includes $C_{1-10}$ alkyl groups, aromatic heterocyclic groups, and $C_{6-14}$ aryl groups. Particularly preferred is $C_{1-3}$ alkyl, furyl, thienyl, benzofuranyl, phenyl, or naphthyl.

Referring to the formula (I), when the substituent on the hydrocarbon or heterocyclic group for R is an alicyclic hydrocarbon group, an aryl group, an aromatic heterocyclic group, or a non-aromatic heterocyclic group, this substituent may be further substituted by one or more, preferably 1 to 3 suitable substituents. As such substituents, there can be mentioned $C_{1-6}$ alkyl groups, $C_{2-6}$ alkenyl groups, $C_{2-6}$ alkynyl groups, $C_{3-7}$ cycloalkyl groups, $C_{6-14}$ aryl groups (e.g. phenyl, naphthyl, etc.), aromatic heterocyclic groups (e.g. thienyl, furyl, pyridyl, oxazolyl, thiazolyl, etc.), non-aromatic heterocyclic groups (e.g. tetrahydrofuryl, morpholino, thiomorpholino, piperidino, pyrrolidino, piperazino, etc.), $C_{7-9}$ aralkyl groups, amino, N-mono($C_{1-4}$)alkylamino groups, N,N-di($C_{1-4}$) alkylamino groups, $C_{2-8}$ acylamino groups (e.g. acetylamino, propionylamino, benzoylamino, etc.), amidino, $C_{2-8}$ acyl groups (e.g. $C_{2-8}$ alkanoyl groups, etc.), carbamoyl, N-mono($C_{1-4}$) alkylcarbamoyl groups, N,N-di($C_{1-4}$)alkylcarbamoyl groups, sulfamoyl, N-mono($C_{1-4}$)alkylsulfamoyl groups, N,N-di ($C_{1-4}$) alkylsulfamoyl groups, carboxyl, $C_{2-8}$ alkoxycarbonyl groups, hydroxy, $C_{1-4}$ alkoxy groups, $C_{2-5}$ alkenyloxy groups, $C_{3-7}$ cycloalkyloxy groups, $C_{7-9}$ aralkyloxy groups, $C_{6-14}$ aryloxy groups (e.g. phenyloxy, naphthyloxy, etc.), mercapto, $C_{1-4}$ alkylthio groups, $C_{7-9}$ aralkylthio groups, $C_{6-14}$ arylthio groups (e.g. phenylthio, naphthylthio, etc.), sulfo, cyano, azido, nitro, nitroso, and halogen (e.g. fluorine, chlorine, bromine, iodine).

In the formula (I), R is preferably a heterocyclic group that may be substituted. More preferably, R is pyridyl, oxazolyl, thiazolyl, or triazolyl group, which may have 1 to 3 substituents selected from $C_{1-3}$ alkyl, furyl, thienyl, benzofuranyl, phenyl, and naphthyl.

Referring to the formula (I), Y represents —CO—, —CH(OH)— or —$NR^3$—. Y is preferably —CH(OH)— or —$NR^3$— and more preferably —$NR^3$—. Referring to an alkyl group that may be substituted for $R^3$, the alkyl group includes $C_{1-4}$ alkyl groups, such as methyl, ethyl, propyl, isopropyl, butyl, isobutyl, sec-butyl, and t-butyl. The substituent includes halogen (e.g. fluorine, chlorine, bromine, iodine), $C_{1-4}$ alkoxy groups (e.g. methoxy, ethoxy, propoxy, butoxy, isobutoxy, sec-butoxy, t-butoxy), hydroxy, amino, $C_{1-4}$ acyl groups (e.g. formyl, acetyl, propionyl, etc.). $R^3$ is preferably $C_{1-4}$ alkyl groups, especially preferably methyl.

The symbol n represents 0, 1 or 2, and is preferably 0 or 1.

X represents CH or N, and is preferably CH.

Referring to the formula (I), A represents a chemical bond or a bivalent aliphatic hydrocarbon group having 1 to 7 carbon atoms. This aliphatic hydrocarbon group may be straight-chain or branched and may further be saturated or unsaturated. Thus, for example, —$CH_2$—, —$CH(CH_3)$—, —$(CH_2)_2$—, —$CH(C_2H_5)$—, —$(CH_2)_3$—, —$(CH_2)_4$—, —$(CH_2)_5$—, —$(CH_2)_6$—, —$(CH_2)_7$—, etc. can be mentioned for the saturated bivalent aliphatic hydrocarbon group, while —CH=CH—, —C($CH_3$)=CH—, —CH=CH—$CH_2$—, —C($C_2H_5$)=CH—, —$CH_2$—CH=CH—$CH_2$—, —$CH_2$—$CH_2$—CH=CH—$CH_2$—, —CH=CH—CH=CH—$CH_2$—, —CH=CH—CH=CH—$CH_2$—, etc. can be mentioned for the unsaturated bivalent aliphatic hydrocarbon group. The symbol A preferably represents a chemical bond or a bivalent aliphatic hydrocarbon group having 1 to 4 carbon atoms, which is preferably a saturated group. More preferably, A represents a chemical bond, —$CH_2$—, or —$(CH_2)_2$—. Still more preferably, A represents a chemical bond or —$(CH_2)_2$—.

The alkyl group for $R^1$ includes $C_{1-4}$ alkyl groups such as methyl, ethyl, propyl, isopropyl, butyl, isobutyl, sec-butyl, and t-butyl. $R^1$ represents preferably hydrogen or methyl, more preferably hydrogen.

Referring to the formula (I), the partial structural formula:

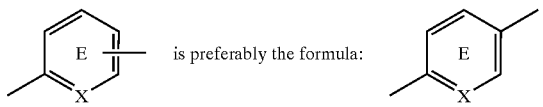

wherein each symbol has the same meaning as defined above.

Furthermore, ring E may optionally have 1 to 4 substituents at substitutable positions. Such substituents include an alkyl group, a hydroxy group that may be substituted, halogen, an acyl group that may be substituted, nitro, and an amino group that may be substituted. These substituents may be the same as the substituents mentioned for the hydrocarbon or heterocyclic group for R.

Ring E, namely the partial structural formula:

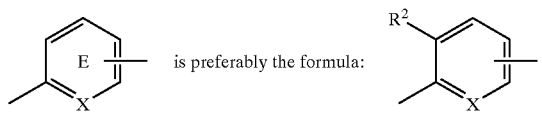

wherein $R^2$ represents hydrogen, an alkyl group, a hydroxy group that may be substituted, halogen, an acyl group that may be substituted, nitro, or an amino group that may be substituted.

The alkyl group, hydroxy group that may be substituted, halogen, acyl group that may be substituted, and amino group that may be substituted, for $R^2$, may each be the same as the substituents mentioned for the hydrocarbon or heterocyclic group for R. Preferably, $R^2$ is hydrogen, hydroxy group that may be substituted, or halogen. More preferably, $R^2$ is hydrogen, a $C_{1-4}$ alkoxy group, or halogen.

Referring to the formula (I), compounds in which a substituent on Ring E and $R^1$ are combined to form a ring include compounds represented by the following formulae.

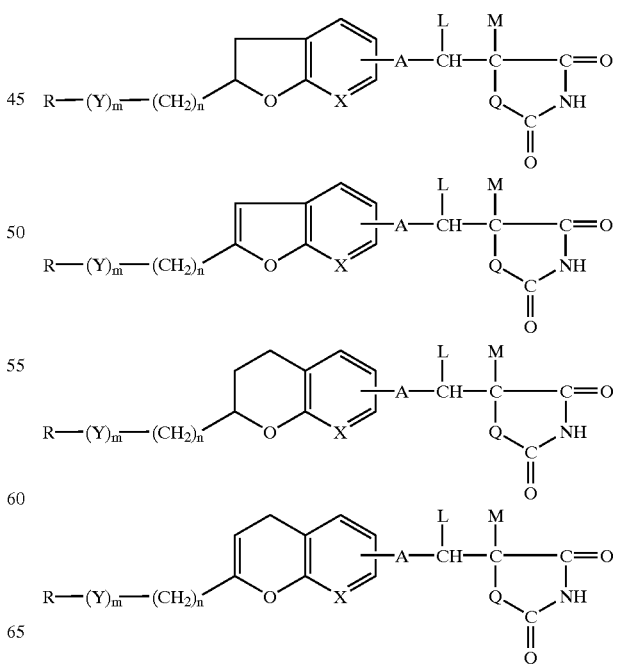

-continued

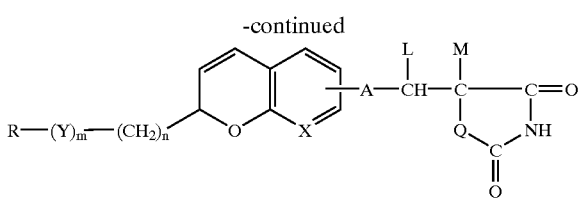

wherein each symbol has the same meaning as defined above.

L and M respectively represent hydrogen or may be combined with each other to form a chemical bond, and preferably they are hydrogen.

Referring to the formula (I), the compound in which L and M are combined with each other to form a chemical bond:

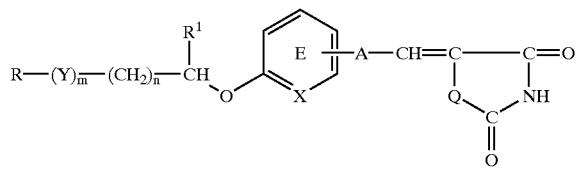

(I-A1)

wherein each symbol has the same meaning as defined above, may exist as (E)- and (Z)-isomers, owing to the double bond at the 5-position of the azolidinedione ring.

The compound in which L and M respectively represent hydrogen:

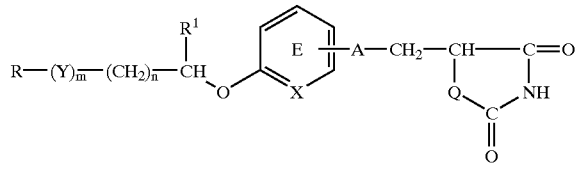

(I-A2)

wherein each symbol has the meaning as defined above, may exist as optical isomers, i.e. (R)- and (S)-forms, with respect to the asymmetric carbon at the 5-position of the azolidinedione ring. This compound includes those optically active compounds, i.e. (R)- and (S)-forms, as well as the racemic form.

The preferred compound represented by the formula (I) includes the compound in which R represents pyridyl, oxazolyl, thiazolyl, or triazolyl group, optionally having 1 to 3 substituents selected from the group consisting of $C_{1-3}$ alkyl, furyl, benzofuranyl, thienyl, phenyl, and naphthyl; Y represents —CH(OH)— or —NR$^3$— wherein R$^3$ is methyl; n is 0 or 1; A represents a chemical bond or —(CH$_2$)$_2$—; R$^1$ represents hydrogen or methyl; ring E, namely the partial structural formula:

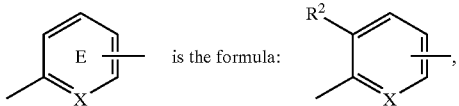

wherein R$^2$ is hydrogen, a $C_{1-4}$ alkoxy group or halogen; and L and M respectively represent hydrogen.

As preferred species of the compound represented by the formula (I), the following compounds are mentioned.

1) 5-[3-[3-fluoro-4-(5-methyl-2-phenyl-4-oxazolylmethoxy)phenyl]propyl]-2,4-oxazolidinedione;
2) 5-[3-[4-[2-[5-methyl-2-(2-naphthyl)-4-oxazolylethoxy]phenyl]propyl]-2,4-oxazolidinedione;
3) 5-[3-[4-[2-(benzo[b]furanyl)-5-methyl-4-oxazoly]methoxylphenyl]propyl]-2,4-oxazolidinedione;
4) 5-[3-[4-[2-(2-furyl)-5-methyl-4-oxazoly]methoxy]-3-methoxyphenyl]propyl]-2,4-oxazolidinedione;
5) 5-[3-[4-[5-methyl-2-(2-naphthyl)-4-oxazoly]methoxylphenyl]propyl]-2,4-oxazolidinedione;
6) 5-[3-[4-(5-methyl-2-phenyl-4-oxazolylmethoxy]phenyl]propyl]-2,4-oxazolidinedione;
7) 5-[2-[2-(5-methyl-2-phenyl-4-oxazolyl)ethoxy]-5-pyridylmethyl]-2,4-thiazolidinedione;
8) 5-[4-[2-(1-methyl-5-phenyl-1,2,4-triazol-3-yl)ethoxy]benzyl]-2,4-thiazolidinedione;
9) 5-[3-[2-(5-methyl-2-phenyl-4-oxazolylmethoxy)-5-pyridyl]propyl]-2,4-thiazolidinedione;
10) 5-[2-(5-methyl-2-phenyl-4-oxazolylmethyl)-5-benzofuranylmethyl]-2,4-oxazolidinedione;
11) 5-[4-[2-hydroxy-2-(5-methyl-2-phenyl-4-oxazolyl)ethoxy]benzyl]-2,4-thiazolidinedione;
12) 5-[4-[2-(5-methyl-2-phenyl-4-oxazolyl)ethoxy]benzyl]-2,4-thiazolidinedione;
13) 5-[[4-[2-(methyl-2-pyridylamino)ethoxy]phenyl]methyl]-2,4-thiazolidinedione (generic name: rosiglitazone);
14) (R)-(+)-5-[3-[4-[2-(2-furyl)-5-methyl-4-oxazolylmethoxy]-3-methoxyphenyl]propyl]-2,4-oxazolidinedione;
15) 5-[2-[2-(5-isopropyl-2-phenyl-4-oxazolyl)ethoxy]-5-pyridylmethyl]-2,4-thiazolidinedione;
16) 5-[3-[3-methoxy-4-[1-(5-methyl-2-phenyl-4-oxazolyl)ethoxy]phenyl]propyl]-2,4-oxazolidinedione;
17) 5-[4-[2-[5-methyl-2-(2-naphthyl)-4-oxazolyl)ethoxy]benzyl]-2,4-oxazolidinedione;
18) 5-[2-[4-[2-[5-methyl-2-(2-naphthyl)-4-oxazolyl)ethoxy]phenyl]ethyl]-2,4-oxazolidinedione;
19) 5-[4-[2-(5-ethyl-2-pyridyl)ethoxy]benzyl]-2,4-thiazolidinedione (generic name: pioglitazone);
20) 5-[[4-[(3,4-dihydro-6-hydroxy-2,5,7,8-tetramethyl-2H-1-benzopyran-2-yl)methoxy]phenyl]methyl]-2,4-thiazolidinedione (generic name: troglitazone).

The above 1) to 20) represent compound Nos. Hereafter, these compounds are sometimes simply referred to as compound No.1, compound No.2, and the like.

Among the above compounds, compound Nos. 13, 14, 19 and 20 are preferred, and compound Nos.13, 19 and 20 are particularly preferred.

The compound represented by the formula (I) (hereafter simply referred to as compound (I)) has an acidic group or a basic group in a molecule, and can form a basic salt or an acid-addition salt. The salt of compound (I) is preferably a pharmacologically acceptable salt, which includes salts with inorganic bases, salts with organic bases, salts with inorganic acids, salts with organic acids, and salts with basic or acidic amino acids.

The preferred salt with an inorganic base includes alkali metal salts such as sodium salt, potassium salt, etc.; alkaline earth metal salts such as calcium salt, magnesium salt, etc.; aluminum salt, and ammonium salts.

The preferred salt with an organic base includes salts with tertiary amines such as trimethylamine, triethylamine, pyridine, picoline, triethanolamine, etc.; salts with secondary amines such as diethanolamine, dicyclohexylamine, N,N'-dibenzylethylenediamine, etc.; and salts with ethanolamine.

The preferred salt with an inorganic acid includes salts with hydrochloric acid, hydrobromic acid, nitric acid, sulfuric acid, phosphoric acid, etc.

The preferred salt with an organic acid includes salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

The preferred salt with a basic amino acid includes salts with arginine, lysine, ornithine, etc. The preferred salt with an acidic amino acid includes salts with aspartic acid, glutamic acid, etc.

The most preferred of all the above-mentioned salts is hydrochloride, sodium salt or potassium salt.

The compound having an insulin sensitivity enhancing activity, for example, the compound (I) or a salt thereof, etc. can be produced in accordance with methods described in JP-A S55(1980)-22636 (EP-A-8203), JP-AS60(1985)-208980 (EP-A-155845), JP-A S61(1986)-286376 (EP-A-208420), JP-A S61(1986)-085372 (EP-A-177353), JP-A S61(1986)-267580 (EP-A-193256), JP-A H5(1993)-86057 (WO-A-9218501), JP-A H7(1995)-82269 (EP-A-605228), JP-A H7(1995)-101945 (EP-A-612743), EP-A-643050, EP-A-710659 (JP-A H9(1997)-194467), etc, or methods analogous thereto.

The compound having an insulin sensitivity enhancing activity which is used in the present invention is not limited as long as it is a compound which restores the impaired insulin receptor function to deblock insulin resistance and consequently enhances insulin sensitivity. Such compound includes the above-described compound represented by the formula (I) or salt thereof.

The compound having an insulin sensitivity enhancing activity other than the above-described one includes, for example, 5-[[3,4-dihydro-2-(phenylmethyl)-2H-1-benzopyran-6-yl]methyl]-2,4-thiazolidinedione (generic name: englitazone) or its sodium salt;

5-[[4-[3-(5-methyl-2-phenyl-4-oxazolyl)-1-oxopropyl]phenyl]methyl]-2,4-thiazolidinedione (generic name: darglitazone/CP-86325) or its sodium salt;

5-(2-naphthalenylsulfonyl)-2,4-thiazolidinedione (AY-31637);

4-[(2-naphthalenyl)methyl]-3H-1,2,3,5-oxathiadiazol-2-oxide (AY-30711);

5-[6-(2-fluorobenzyloxy)naphthalene-2-ylmethyl]-2,4-thiazolidinedione (MCC-555);

5-(2,4-dioxothiazolidin-5-ylmethyl)-2-methoxy-N-[4-(trifluoromethyl)benzyl]benzamide (KRP-297);

(Z)-1,4-bis-4-[(3,5-dioxo-1,2,4-oxadiazolidin-2-yl)methyl]phenoxybut-2-ene (YM440);

4-[4-[2-(5-methyl-2-phenyl-4-oxazolyl)ethoxy]benzyl]-3,5-isoxazolidinedione (JTT-501).

An apoptosis inhibitory activity is evaluated, for instance, by adding a test compound to a system in which apoptosis is caused, determining an apoptosis activity, and calculating an inhibitory ratio of the apoptosis activity. Methods for determining the apoptosis activity include 1) a method which comprises inducing apoptosis by adding actinomycin D to cells, and quantitating DNA ladders of cells [M. Hermann et al., Nucleic Acids Research, vol. 22, p. 5506 (1994); Y. A. Ioannou and F. W. Chen, Nucleic Acids Research, vol. 24, p. 992 (1996)]; 2) a method which comprises adding TNF-α to cells, and determining the cell death [Meneki Jikken Sousahou II, edited by S. Migita, S. Konda, T. Honjyo and T. Hamaoka, Nankoudou, pp. 861-871 (1995)]; and the like.

As the apoptosis inhibitor of the present invention, "the compound having an insulin sensitivity enhancing activity", for example, "the compound (I) or salt thereof" as such can be used. Usually, the apoptosis inhibitor can be produced in accordance with a per se known means as a method for producing a pharmaceutical composition by using "the compound having an insulin sensitivity enhancing activity", for example,"the compound (I) or salt thereof" together with pharmaceutically acceptable carriers, and the like. Specifically, the apoptosis inhibitor is obtained by admixing the compound (I) or salt thereof with carriers in a conventional manner, and may be used in the form of a pharmaceutical composition.

As the pharmaceutically acceptable carrier, a variety of organic and inorganic carriers in common use as raw materials for pharmaceutical preparations are employed. The carrier is formulated in the form of the excipient, lubricant, binder, and disintegrator for a solid dosage form; and the solvent, solubilizer, suspending agent, isotonizing agent, buffering agent and local analgesic for a liquid dosage form. When necessary, pharmaceutical additives such as the preservative, antioxidant, coloring agent, sweetener, etc. can also be used.

The preferred excipient includes lactose, sucrose, D-mannitol, xylitol, sorbitol, erythritol, starch, crystalline cellulose, light silicic anhydride, etc.

The preferred lubricant includes magnesium stearate, calcium stearate, talc, colloidal silica, etc.

The preferred binder includes pregelatinized starch, methyl cellulose, crystalline cellulose, sucrose, D-mannitol, trehalose, dextrin, hydroxypropylcellulose, hydroxypropylmethylcellulose, polyvinylpyrrolidone, etc.

The preferred disintegrator includes starch, carboxymethylcellulose, low-substituted hydroxypropylcellulose, carboxymethylcellulose calcium, croscarmellose sodium, carboxymethylstarch sodium, etc.

The preferred solvent includes water for injection, alcohol, propylene glycol, macrogol, sesame oil, corn oil, tricaprylin, etc.

The preferred solubilizer includes polyethylene glycol, propylene glycol, D-mannitol, trehalose, benzyl benzoate, ethanol, trisaminomethane, cholesterol, triethanolamine, sodium carbonate, sodium citrate, etc.

The preferred suspending agent includes surfactants such as stearyltriethanolamine, sodium lauryl sulfate, laurylaminopropionic acid, lecithin, benzalkonium chloride, benzethonium chloride, glyceryl monostearate, etc.; and hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose, etc.

The preferred isotonizing agent includes sodium chloride, glycerin, D-mannitol, etc.

The preferred buffering agent includes buffer solutions such as phosphate, acetate, carbonate, citrate, etc.

The preferred local anesthetic includes benzyl alcohol, etc.

The preferred antiseptic includes p-hydroxybenzoic acid esters, chlorobutanol, benzyl alcohol, phenethyl alcohol, dehydroacetic acid, sorbic acid, etc.

The preferred antioxidant includes salts of sulfurous acid, ascorbic acid, etc.

The content of "the compound having an insulin sensitivity enhancing activity" or "the compound (I) or salt thereof" in the apoptosis inhibitor of the present invention is about 5 to about 100 weight %, preferably about 10 to about 80 weight %.

The apoptosis inhibitor of the present invention can be manufactured by conventional methods in the pharmaceutical preparation techniques, for example methods described in the Japanese Pharmacopoeia (e.g., Thirteenth Edition).

Examples of dosage forms of the apoptosis inhibitor of the present invention include oral dosage forms such as tablets, capsules (inclusive of soft capsules and microcapsules), powders, granules, and syrups; and non-oral dosage forms such as injections, suppositories, pellets, and drip infusions. These dosage forms are low in the toxic potential, and can be safely administered either orally or non-orally.

The apoptosis inhibitor of the present invention can be used as an agent for prophylaxis and treatment of a disease mediated by promotion of apoptosis in mammals (e.g., man, mouse, rat, rabbit, dog, cat, bovine, equine, swine, monkey, etc.).

Examples of such diseases include viral diseases such as AIDS and fulminant hepatitis; neurodegenerative diseases such as Alzheimer's disease, Parkinson's disease, amyotrophic lateral sclerosis, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint diseases such as osteoarthritis; atherosclerosis; and etc. The apoptosis inhibitor of the present invention is especially preferably used as an agent for prophylaxis or treatment of a neurodegenerative disease.

The dosage of the apoptosis inhibitor of the present invention differs depending on the subject, route of administration, clinical condition, etc. For oral administration to an adult patient suffering from a neurodegenerative disease, for instance, the usual unit dose is about 0.1 mg/kg to about 30 mg/kg, preferably about 2 mg/kg to about 20 mg/kg, as an active ingredient, "the compound having an insulin sensitivity enhancing activity", for instance, "the compound (I) or salt thereof". This dose is preferably administered once to 3 times a day.

BEST MODE FOR CARRYING OUT THE INVENTION

The following examples and test examples are intended to describe the present invention in further detail and should by no means be construed as defining the scope of the invention.

EXAMPLE 1

A fluidized-bed granulating and drying machine (produced by Powerex, Japan) was charged with 2479.5 g of hydrochloride of Compound No. 19 (2250 g in terms of Compound No. 19), 13930.5 g of lactose and 540 g of carboxymethylcellulose calcium (carmellose calcium), followed by mixing at the preheating temperature and spraying 7500 g of an aqueous solution containing 450 g of hydroxypropylcellulose to yield granules. 16820 g of the granules were processed with cutter-mill (produced by Showa Kagaku Kikai Kousakusho, Japan) to yield milled granules. 16530 g of the milled granules, 513 g of carmellose calcium and 57 g of magnesium stearate were mixed to yield lubricated powders by using tumbling mixer (produced by Showa Kagaku Kikai Kousakusho, Japan). 16800 g of the lubricated powders were tabletted by using tabletting machine (produced by Kikusui Seisakusho; Japan) to yield 140000 tablets having the following composition and each containing 15 mg of Compound No. 19.

| Composition per tablet (Unit: mg): | |
| --- | --- |
| 1) Hydrochloride of Compound No. 19 | 16.53 |
| 2) Lactose | 92.87 |
| 3) Carmellose calcium | 7.2 |
| 4) Hydroxypropylcellulose | 3.0 |
| 5) Magnesium stearate | 0.4 |
| Total: | 120.0 |

EXAMPLE 2

In substantially the same manner as in Example 1, 140000 tablets having the following composition and each containing 30 mg of Compound No. 19 were obtained.

| Composition per tablet (Unit: mg): | |
| --- | --- |
| 1) Hydrochloride of Compound No. 19 | 33.06 |
| 2) Lactose | 76.34 |
| 3) Carmellose calcium | 7.2 |
| 4) Hydroxypropylcellulose | 3.0 |
| 5) Magnesium stearate | 0.4 |
| Total: | 120.0 |

EXAMPLE 3

In substantially the same manner as in Example 2, 140000 tablets having the following composition and each containing 45 mg of Compound No. 19 were obtained.

| Composition per tablet (Unit: mg): | |
| --- | --- |
| 1) Hydrochloride of Compound No. 19 | 49.59 |
| 2) Lactose | 114.51 |
| 3) Carmellose calcium | 10.8 |
| 4) Hydroxypropylcellulose | 4.5 |
| 5) Magnesium stearate | 0.6 |
| Total: | 180.0 |

TEST EXAMPLE 1

Apoptosis (cell death) was induced by adding TNF-α to cells. The inhibitory activity of a test compound to this apoptosis was determined by using known dexamethasone having an apoptosis inhibitory activity as the standard.

Namely, 25 µl of a culture medium (PRMI-1640, produced by Nikken Seibutsu Igaku Kenkyusho, Japan) (containing 10 weight % of fetal bovine serum) was added to each well of a 96-well microplate. Then, added was 2 µl of a solution prepared by 20 volume fold dilution of dimethylformamide (in the case of Compound No. 16) or dimethylsulfoxide (in the case of Compound Nos. 2, 4, 6, 8, 13) solution of a test compound (concentration of the test compound: 1 mM) with the above culture medium.

Subsequently, 25 µl of a solution prepared by dissolving TNF-α (Genzyme, USA)(40 ng/ml culture medium) in the above culture medium, and 50 µl of a suspension ($2 \times 10^5$ cells/ml) prepared by suspending mouse fibroblast (L929 cells, IFO 50409) in the above culture medium were added, and then cells were cultivated for 72 hours at 37° C. in the presence of 5% carbon dioxide in air. The final concentration of the test compound during cultivation was 1 μM.

After cultivation, the culture medium was removed from the wells by aspiration, and 50 μl of a 5% (w/v) crystal violet/70% (v/v) methanol solution was added to each well to pigment the living cells. Then the wells were washed and dried. The apoptosis inhibitory activity of the test compound was obtained by determining the optical density by using an absorptiometer [Microplate Reader Model 450, produced by Bio-Rad] at the wavelength of 570 nm.

While, the apoptosis inhibitory activity of dexamethasone was obtained in the same manner as above except that the above test compound (final concentration: 1 μM) was replaced by dexamethasone (final concentration: 1.1 μM).

Then, the apoptosis inhibitory activity of each test compounds (final concentration: 1 μM) was calculated when the apoptosis inhibitory activity of dexamethasone (final concentration: 1.1 μM) was 100.

The results are shown in Table 1.

TABLE 1

| Apoptosis inhibitory activity (%) | |
|---|---|
| Test compound | Apoptosis inhibitory activity (%) |
| Compound No. 2 | 70 |
| Compound No. 4 | 74 |
| Compound No. 6 | 70 |
| Compound No. 8 | 70 |
| Compound No. 13 | 92 |
| Compound No. 16 | 71 |

It is apparent from Table 1 that the compound (I) used in the present invention inhibited apoptosis.

INDUSTRIAL APPLICABILITY

The apoptosis inhibitor of the present invention shows an excellent apoptosis inhibitory activity, and is useful as an agent for prophylaxis and treatment of diseases mediated by promotion of apoptosis, such as viral diseases, neurodegenerative diseases, myelodysplasis, ischemic diseases and hepatic diseases.

What is claimed is:

1. A method for inhibiting apoptosis in a mammal comprising administering to said mammal an effective amount of 5-(2,4-dioxothiazolidin-5-ylmethyl)-2-methoxy-N-[4-(trifluoromethyl)benzyl]benzamide, or a pharmaceutically acceptable salt thereof.

2. A method for treating or preventing disease mediated by promotion of apoptosis, in a mammal in need thereof, comprising administering to said mammal an effective amount of 5-(2,4-dioxothiazolidin-5-ylmethyl)-2-methoxy-N-[4-(trifluoromethyl)benzyl]benzamide, or a pharmaceutically acceptable salt thereof.

3. A method of claim 2, wherein the disease mediated by promotion of apoptosis is Alzheimer's disease.

4. A method of claim 2, wherein the disease mediated by promotion of apoptosis is Parkinson's disease.

5. A method of claim 2, wherein the disease mediated by promotion of apoptosis is myelodysplasis.

6. A method of claim 2, wherein the disease mediated by promotion of apoptosis is ischemic disease.

7. A method of claim 2, wherein the disease mediated by promotion of apoptosis is hepatic disease.

8. A method of claim 2, wherein the disease mediated by promotion of apoptosis is joint disease.

9. A method of claim 2, wherein the disease mediated by promotion of apoptosis is arteriosclerosis.

10. A method of claim 6, wherein the ischemic disease is myocardial infarction.

* * * * *

UNITED STATES PATENT AND TRADEMARK OFFICE
CERTIFICATE OF CORRECTION

| | | |
|---|---|---|
| PATENT NO. | : 6,555,565 B2 | Page 1 of 1 |
| DATED | : April 29, 2003 | |
| INVENTOR(S) | : Junji Matsui et al. | |

It is certified that error appears in the above-identified patent and that said Letters Patent is hereby corrected as shown below:

Title page, Item [62] and Column 1, lines 3-10,
Should be corrected to read:
-- This application is a divisional of U.S. Patent Application Serial No. 09/519,274, filed March 7, 2000 and now U.S. Patent 6,399,639 granted 06/04/2002, which was a continuation of U.S. Patent Application serial No. 09/272,747 filed March 15, 1999, now U.S. Patent 6087384 granted 7/11/2000, which was the National Phase of International Application for Patent Serial No. PCT/JP98/05178 filed November 18, 1998. --

Title page,
Item [60], Related U.S. Application Data, should be deleted.

Signed and Sealed this

Seventeenth Day of February, 2004

JON W. DUDAS
*Acting Director of the United States Patent and Trademark Office*